United States Patent [19]

Mack et al.

[11] Patent Number: Plant 6,403

[45] Date of Patent: Nov. 15, 1988

[54] CHRYSANTHEMUM PLANT NAMED GINGER

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 938,860

[22] Filed: Dec. 8, 1986

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Ginger particularly characterized by its flat capitulum form; decorative capitulum type; yellow to yellow-orange ray floret color with bronze-red center; diameter across face of capitulum of up to 5.5 cm at maturity; short plant height with spreading and prolific branching pattern; average natural season flower date of August 26 in Salinas, Calif. and September 24 in Hightstown, N.J.; uniform seven week photoperiodic flowering response to short days in photoperiodic controlled flowering programs; and by its durable, uniform performance in outside fall flowerings and in spring small pot flowering programs.

3 Drawing Sheets

The present invention comprises a new and distinct cultivar of chrysanthemum, botanically known as *Chrysanthemum morifolium,* Ramat., and referred to by the cultivar name Ginger.

Ginger, identified as 82M18017, was originated from a cross made by Grace H. Mack in a controlled breeding program in New Canaan, Conn., in 1981. The parents of Ginger were both unnamed seedlings.

Ginger was discovered and selected as one flowering plant within the progeny of the stated cross by Cornelis P. VandenBerg in September 1982, in a controlled environment in Salinas, Calif.

The first act of asexual reproduction of Ginger was accomplished when vegetative cuttings were taken from the initial selection in December 1982 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Ginger are firmly fixed and are retained through successive generations of asexual reproduction.

Ginger has not been observed under all possible environmental conditions. The phenotype may vary significantly with variations in environment such as temperature, light intensity, and daylength.

The following observations, measurements and comparisons describe plants grown in controlled open areas in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Ginger, which, in combination, distinguish this Chrysanthemum as a new and distinct cultivar:

1. Flat capitulum form.
2. Decorative capitulum type.
3. Yellow to yellow-orange ray floret color with bronze-red center.
4. Diameter across face of capitulum up to 5.5 cm at maturity.

5. Short plant height.
6. Spreading and prolific branching pattern.
7. Average natural season flower date of August 26 in Salinas, Calif., and September 24 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Ginger, with the colors being as nearly true as possible with illustrations of this type.

Sheet 1 is a color photograph of Ginger grown as a pinched spray pot mum.

Sheet 2 is a black and white photograph of three views of the inflorescence of Ginger.

Sheet 3 is a black and white photograph showing the upper and under sides of the leaves of Ginger at three stages of development (mature, intermediate and immature).

Of the commercial cultivars known to the inventors, the most similar in comparison to Ginger is Revere, discosed in U.S. Plant Pat. No. 4,005. Reference is made to attached Chart A, which compares certain characteristics of Ginger to the same characteristics of Revere.

Similar traits are capitulum form and type, controlled flowering response period, and a contrasting bronze-red center of capitulum. Ginger has a more spreading and prolific branching pattern, more extensively yellow to yellow-orange ray florets, smaller diameter across face of capitulum, shorter plant height, and a slightly earlier natural season flowering response in comparison with Revere.

In the following description, color references are made to the Royal Horticultural Society Colour Chart. The exact color for the corolla of ray florets of the center of the capitulum of Ginger is not represented in the R.H.S. Colour Chart, and the color values given are those closest to the actual color. The color values were determined on plant material grown outside in Salinas, Calif. on Aug. 25, 1986.

Classification:

*Botanical.*—*Chrysanthemum morifolium,* Ramat., cv. Ginger.

*Commercial.*—Decorative spray pot mum and garden mum.

INFLORESCENCE

A. Capitulum:

*Form.*—Flat.

*Type.*—Decorative.

*Diameter across face.*—Up to 5.5 cm at maturity.

B. Corolla of ray florets:

*Color (general tonality from a distance of three meters).*—Yellow to yellow-orange with bronze-red center.

*Color (upper surface).*—12A to 14A, with center of capitulum closest to 169A to 169C.

*Color (under surface).*—12B to 14C.

*Shape.*—Oblong.

C. Corolla of disc florets: Not present.

D. Reproductive organs:

*Androecium.*—Not present.

*Gynoecium.*—Present on ray florets.

PLANT

A. General appearance:

*Height.*—Short.

*Branching pattern.*—Spreading and prolific.

B. Foliage:

*Color (upper surface).*—137A to 137B.

*Color (under surface).*—137B to 137C.

*Shape.*—Lobed and slightly serrated.

CHART A

COMPARISON OF GINGER AND REVERE

| CULTIVAR | RAY FLORET COLOR | CAPITULUM FORM AND TYPE | BRANCHING PATTERN |
|---|---|---|---|
| GINGER | YELLOW TO YELLOW-ORANGE WITH BRONZE-RED CENTER | FLAT | SPREADING |
| REVERE | RED BRONZE TO YELLOW-BRONZE | FLAT DECORATIVE | SEMI UPRIGHT |

CHART A-continued

COMPARISON OF GINGER AND REVERE

| CULTIVAR | DIAMETER ACROSS FACE OF CAPITULUM | PLANT HEIGHT | AVERAGE NATURAL SEASON FLOWER DATE SALINAS, CALIFORNIA |
|---|---|---|---|
| GINGER | UP TO 5.5 cm. | SHORT | AUGUST 26 |
| REVERE | UP TO 7 cm. | MEDIUM | AUGUST 28 |

| CULTIVAR | AVERAGE NATURAL SEASON FLOWER DATE HIGHTSTOWN NEW JERSEY | CONTROLLED RESPONSE |
|---|---|---|
| GINGER | SEPTEMBER 24 | 7 WEEKS |
| REVERE | SEPTEMBER 27 | 7 WEEKS |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

We claim:

1. A new and distinct Chrysanthemum plant named Ginger, as described and illustrated, and particularly characterized as to uniqueness by the combined characteristics of flat capitulum form; decorative capitulum type; yellow to yellow-orange ray floret color with bronze-red center; diameter across face of capitulum of up to 5.5 cm at maturity; short plant height with spreading and prolific branching pattern; average natural season flower date of August 26 in Salinas, Calif. and September 24 in Hightstown, N.J.; uniform seven week photoperiodic flowering response to short days in photoperiodic controlled flowering programs; and durable, uniform performance in outside fall flowerings and in spring small pot flowering programs.

* * * * *

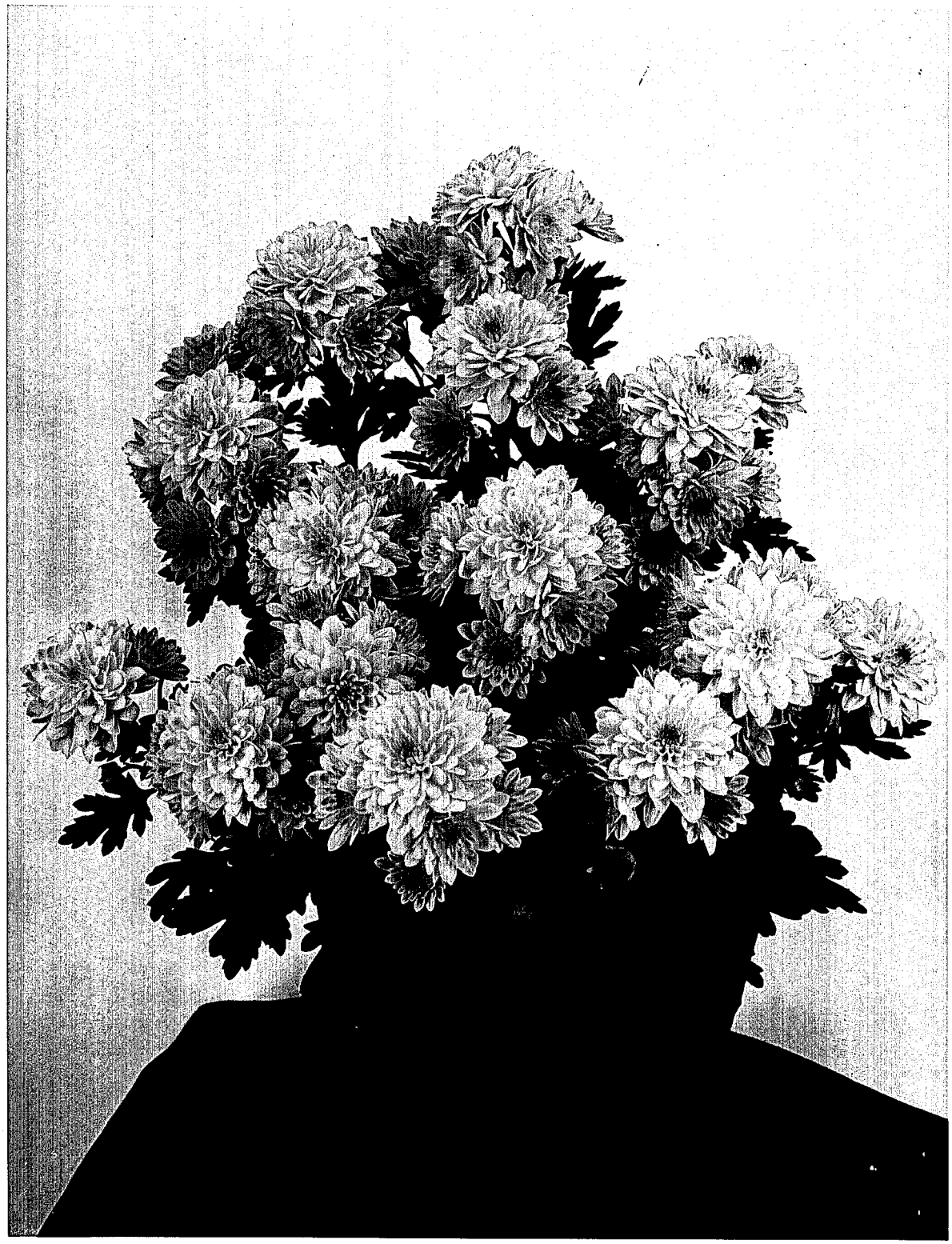

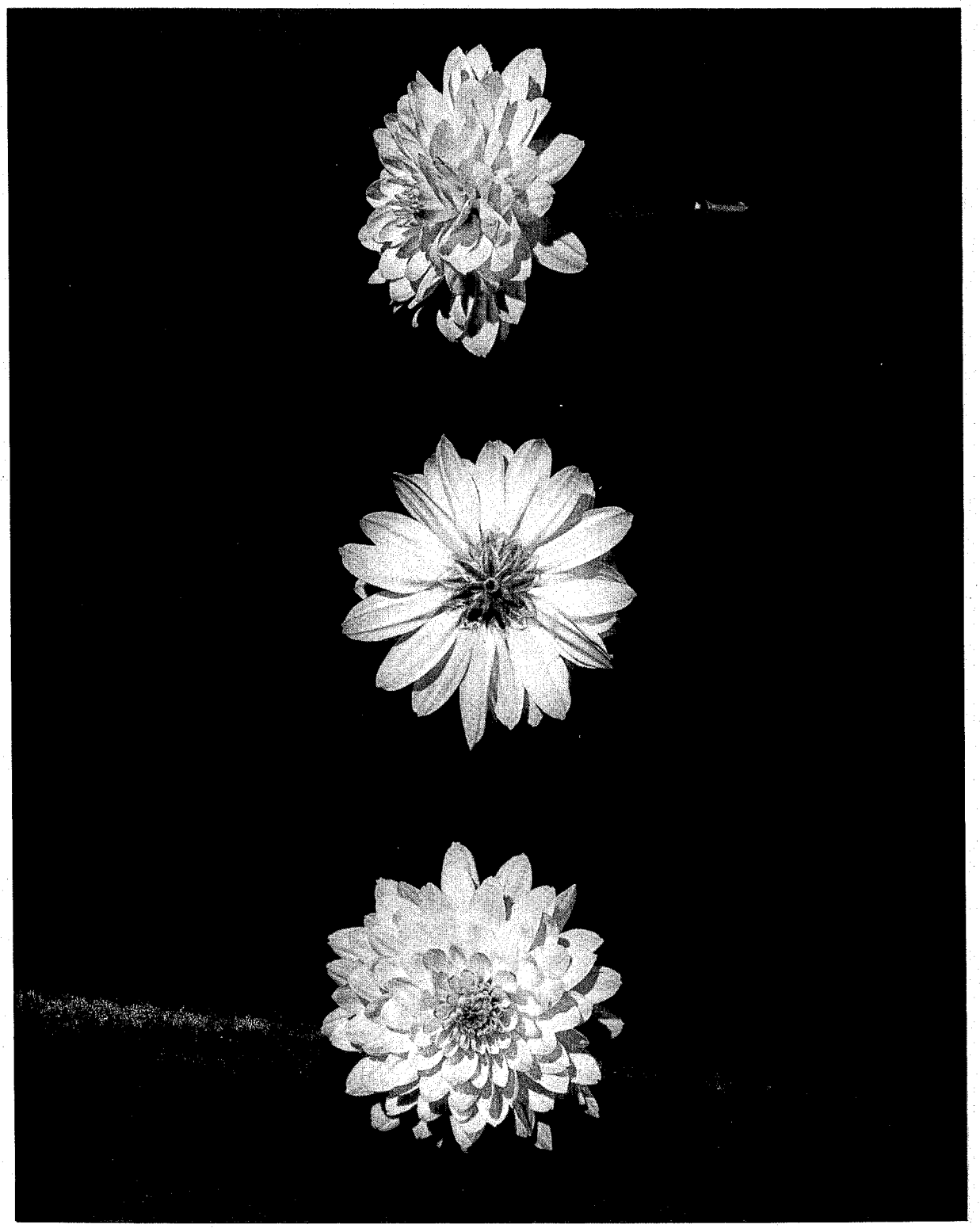

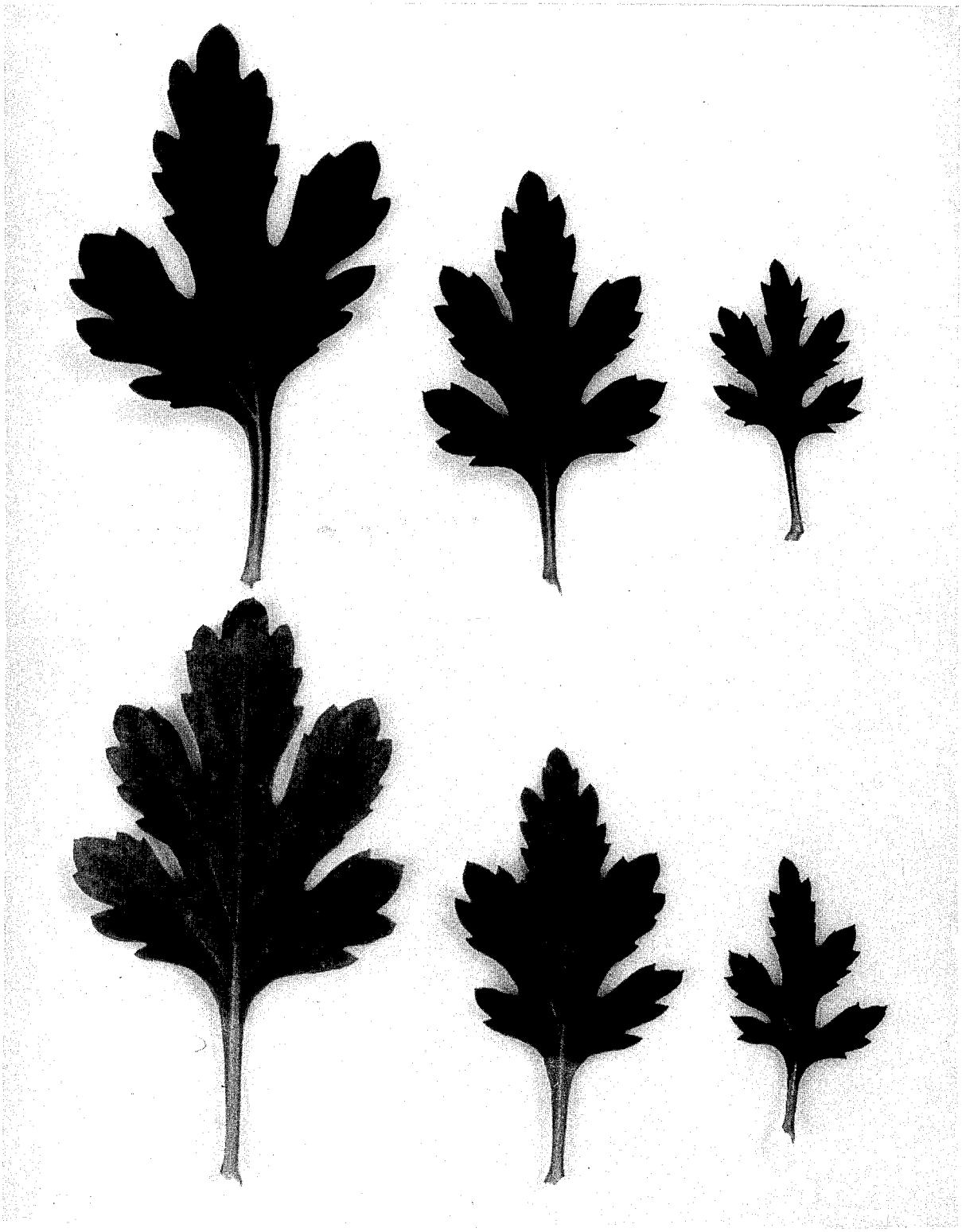

UNITED STATES PATENT AND TRADEMARK OFFICE

CERTIFICATE OF CORRECTION

PATENT NO. : PP 6,403

DATED : November 15, 1988

INVENTOR(S) : Grace H. Mack and Cornelis P. VandenBerg

It is certified that error appears in the above—identified patent and that said Letters Patent is hereby corrected as shown below:

Column 3, Line 44, Chart a:

Under the heading "Capitulum Form and Type", the cultivar Ginger should be described as "Flat, Decorative".

Under the heading "Branching Pattern", the cultivar Ginger should be described as "Spreading and Prolific".

Signed and Sealed this

Twenty-sixth Day of June, 1990

*Attest:*

HARRY F. MANBECK, JR.

*Attesting Officer*

*Commissioner of Patents and Trademarks*